United States Patent [19]

Egerton

[11] 3,956,488

[45] May 11, 1976

[54] COMPOSITIONS AND METHODS FOR THE TREATMENT OF HELMINTHIASIS

[75] Inventor: John R. Egerton, Neshanic Station, N.J.

[73] Assignee: Merck & Co., Inc., Rahway, N.J.

[22] Filed: Sept. 27, 1973

[21] Appl. No.: 401,499

[52] U.S. Cl. ............................... 424/232; 424/270
[51] Int. Cl.² ........................................ A61K 31/625
[58] Field of Search ................... 424/230, 232, 270

[56] References Cited
UNITED STATES PATENTS 3,743,738  7/1973  Hoff et al. ........................... 424/270
3,798,258  3/1974  Patchett et al. ..................... 260/479 R

*Primary Examiner*—V. D. Turner
*Attorney, Agent, or Firm*—David L. Rose; J. Jerome Behan

[57] ABSTRACT

Compositions and methods for the treatment of helminthiasis are disclosed which utilize 5-isopropoxycarbonylamino-2-(4'-thiazolyl)-benzimidazole and 3'-chloro-4'-(p-chlorophenoxy)-3,5-diiodosalicylanilide as the active ingredients.

8 Claims, No Drawings

COMPOSITIONS AND METHODS FOR THE TREATMENT OF HELMINTHIASIS

SUMMARY OF THE INVENTION

This invention relates to new compositions of matter useful in anthelmintic therapy and to methods of employing such compositions in the treatment and control of helminthiasis. More particularly this invention concerns pharmaceutical formulations containing an anthelmintically effective combination of a salicylanilide and a 2-substituted benzimidazole and methods of employing such formulations. Specifically this invention relates to compositions and methods as mentioned above wherein the anthelmintically active compounds are 5-isopropoxycarbonylamino-2-(4'-thiazolyl)-benzimidazole and 3'-chloro-4'-(p-chlorophenoxy)-3,5-diiodosalicylanilide.

Helminthiasis is a widely occurring disease affecting animals, including humans, and causes large economic losses in the domesticated animal industry. Particularly susceptibel to the disease are ruminants such as sheep, cattle, and goats and equines such as horses and mules. In view of the large economic interest in the prevention and control of helminthiasis, modernday research is directed to providing new classes of anthelmintically active materials and finding ways for improving the efficacy of the currently known anthelmintic agents.

It is accordingly an object of the present invention to provide compositions possessing a high degree of anthelmintic activity. Another object is to provide compositions containing anthelmintically active substituted benzimidazoles and substituted salicylanilides. Specifically it is an object of this invention to provide an anthelmintically active composition containing a combination of 5-isopropoxycarbonylamino-2-(4'-thiazolyl)-benzimidazole and 3'-chloro-4'-(p-chlorophenoxy)-3,5-diiodosalicylanilide. Yet a further object is to provide methods for treating helminthiasis with the aforementioned combination compositions with the substantial absence of significant toxic effects. Still another object is to provide a method for treating helminthiasis with a combination of a substituted benzimidazole and a substituted salicylanilide wherein activity of said combination composition is significantly enhanced. Further objects will become apparent upon reading the complete description which follows.

According to the present invention, it has been surprisingly discovered that the anthelmintic activity of 5-isopropoxycarbonylamino-2-(4'-thiazolyl)-benzimidazole can be greatly enhanced when it is administered to the host animal substantially concurrently or in combination with 3'-chloro-4'-(p-chlorophenoxy)-3,5-diiodosalicylanilide.

With regard to the individual amounts of the 2-substituted benzimidazole and the substituted salicylanilide present in the composition, such amounts should be sufficient to provide an effective dosage for the proper treatment of the parasitic disease. These amounts will vary depending on the mode of treatment, the size of the host, and the severity of the infection. The compositions are highly effective against the important strongyles, trichostrongyles, fasciolids, and other helminths, commonly found in sheep and cattle and other large animals.

Each component need not be present at such dosage levels as to be fully anthelmintically active itself, it having been discovered that the compounds will exercise their enhancing effect even when employed at levels which, if used alone, would not be optimally effective in the host. Generally, when single unit dosage forms such as tablets, boluses, drenches, or parenteral forms are desired to be administered to the animal, suitable results are obtained when the compositions contain enough of each ingredient such that a broad spectrum of activity and efficacy is achieved with a minimum of toxic side effects.

The combined amounts of each compound in the composition, as well as the remaining constituents of the composition, will vary according to the type of treatment to be employed, the host animal, and the particular parasitic disease being treated. In general, however, compositions containing a total weight percent of the benzimidazole and the salicylanilide ranging from 0.001 to 95% will be suitable with the remainder being any suitable carrier or vehicle. Within this range the relative amounts of the benzimidazole compound and the salicylanilide compound is not critical except to the extent that the resulting composition is pharmaceutically effective. When the compositions are to be solid unit dosage forms as in tablets or boluses the ingredients other than the benzimidazole and salicylanilide compounds may be any other acceptable vehicles convenient in the preparation of such forms, and preferably materials nutritionally suitable such as starch, lactose, talc, magnesium stearate, vegetable gums, and the like. In such forms the combined amounts of anthelmintic ingredients conveniently ranges from about 5 to 80% by weight of the total composition.

When the unit dosage form is in the form of a drench, the benzimidazole and salicylanilide compounds may be mixed with agents which will aid in the subsequent suspending of the anthelmintic ingredients in water, such as bentonite, clays, water soluble starches, cellulose derivatives, gums, surface active agents and the like to form a predrench composition which is added to water just before use. In the predrench formulation, in addition to the suspending agent, such ingredients as preservatives, antifoaming compounds, and the like may be employed. Such a dry product may contain over 95% by weight of the anthelmintic compounds, the rest being contributed by excipients. Preferably the solid composition contains from 30 to 95% by weight of the combined weights of the benzimidazole and the salicylanilide compounds. Enough water should be added to the solid product to provide the proper dosage level within a convenient amount of liquid for a single oral dose. A commonly used measure in the field is one fluid ounce of material and thus that one fluid ounce of material should contain enough of the compounds to provide the effective dosage level. Liquid drench formulations containing from about 10 to 80 weight percent of dry ingredients will in general be suitable with the preferred range being from 15 to 50 weight percent.

When the composition is to be employed for parenteral administration, the active ingredients are suitably admixed with an acceptable oil base vehicle, preferably of the vegetable oil variety such as peanut oil, cottonseed oil and the like. In such formulations, the active compounds conveniently range from about 5 to 80% by weight of the total composition.

Where the compositions are intended to be used as feeds, feed supplements, or feed premixes, they will be mixed with suitable ingredients of an animal's nutrient ration. The solid orally ingestible carriers normally used for such purposes, such as distillers' dried grains, corn meal, citrus meal, fermentation residues, ground oyster shells, Attapulgus clay, wheat shorts, molasses solubles, corn cob meal, edible vegetable substances, toasted dehulled soya flour, soybean mill feed, antibiotic mycelia, soya grits, crushed limestone, and the like are all suitable. The anthelmintic agents are intimately dispersed or admixed throughout the solid inert carrier by methods such as grinding, stirring, milling, or tumbling. By selecting proper diluents and by altering the ratio of carrier to active ingredient, compositions of any desired concentration may be prepared. Feed supplement formulations containing from about 5% to about 50% by weight, and preferably from about 10–30% by weight of active ingredients are particularly suitable for addition to feeds. The active compounds are normally dispersed or mixed uniformly in the diluent but in some instances may be adsorbed on the carrier.

These supplements are added to the finished animal feed in an amount adequate to give the final concentration desired for controlling or treating helminthiasis by way of the animal ration. Although the preferred level in feeds will depend on the particular compounds being employed, the combined weights of benzimidazole and substituted salicylanilide of this invention are normally fed at levels of 0.05–25% in the feed. Where the treatment is prophylactic, smaller amounts may be employed, suitably of the order of 0.001–3.0 weight percent based on the weight of feed, and may be administered over prolonged periods. An advantageous method of administering the compositions of this invention to animals whose feeds are conveniently pelleted, such as sheep, is to incorporate them directly in the pellets. For instance, the compositions of the present invention are readily incorporated in nutritionally adequate alfalfa pellets (during the pelleting operation) at levels of about 2 to 110 grams per pound of pellets for therapeutic use, and at lower levels for prophylactic use, and such pellets fed to the worm-infected animals. Alternatively, the anthelmintic compositions may be incorporated in salt licks or salt blocks at any desired concentration (concentrations of 5–25% by weight are conveniently employed). Large animals, such as sheep and cattle, then receive the anthelmintics with their salt.

As stated previously, a preferred mode of administering the substituted salicylanilide with the 2-substituted benzimidazole is to formulate them together into a single composition. It is, however, an added feature of the invention that the two compounds need not be administered simultaneously in one formulation. They may be administered separately, each in its own formulation if desired, to obtain the enhancing action of the combination, provided that the administration of each is performed within such period of time as will allow the beneficial interaction between the benzimidazole and salicylanilide against the helminths. This period of time will vary between different species of animal, however, administration of one compound within as much as six hours of the other may be performed. If this mode of operation is practiced, the period is preferably not more than one hour.

5-Isopropoxycarbonylamino-2-(4'-thiazolyl)-benzimidazole is readily prepared by reacting 5-amino-2-(4'-thiazolyl)-benzimidazole with isopropylhaloformate, preferably isopropylchloroformate. The reaction is conveniently conducted at temperatures of from about 20°–50°C. in an organic solvent and in the presence of an acid binding agent. It has been found very convenient to conduct the reaction in a solvent such as pyridine which also serves as the acid binding agent although other basic solvents such as the picolines and lutidines could be employed equally well. Neutral solvents, however, can be employed in which case the product is isolated as the acid addition salt. The resulting carbamate is water insoluble and is conveniently precipitated by diluting the reaction mixture with a relatively large volume of water. The solid product is then recovered by standard methods and purified by recrystallization from solvents such as methanol, ethanol, acetonitrile, and the like, or from mixtures thereof.

3'-Chloro-4'-(p-chlorophenoxy)-3,5-diiodosalicylanilide is prepared by condensing 3,5-diiodosalicylic acid halide with 3-chloro-4-(p-chlorophenoxy)-aniline. Generally the salicylic acid halide is formed from the salicylic acid compound in the presence of a solvent and said salicylic acid halide reacted in situ with the aniline compound. Suitable solvents are benzene, toluene, chlorobenzene, chloroform, carbon tetrachloride, dioxane, and the like. The salicylic acid halide is preferably formed from the salicylic acid compound and thionyl chloride, thionyl bromide, phosphorous trichloride, phosphorous oxychloride, and like halogenating agents. The temperature of the halogenation reaction is not critical, suitable results being obtained at temperatures ranging from room temperature to the reflux temperature of the reaction mixture. It is preferred to conduct the reaction at the reflux temperature in order to facilitate the reaction.

While the reaction may be performed by combining the salicylic acid compound, the aniline compound, and the halogenating agent in one step, it is also possible to prepare and isolate the salicylic acid halide and react it separately with the aniline compound. In such a situation the aniline compound and the acid halide are combined in a solvent as listed above, to which is added a base in order to react with the hydrogen halide liberated during the course of the reaction. The reaction mixture is then neutralized with dilute acid such as hydrochloric acid and the solid which separates is filtered off and purified by techniques known to those skilled in this art.

The particular ratio of each compound to the other in the composition is not critical and generally any anthelmintically effective quantity of each compound may be administered. In general, it has been found preferably to administer compositions to infected animals such that from 2½ to 50 mg/kg of animal body weight of 5-isopropoxycarbonylamino-2-(4'-thiazolyl)-benzimidazole is administered along with from 1 to 45 mg/kg of animal body weight of 3'-chloro-4'-(p-chlorophenoxy)-3,5-diiodosalicylanilide. It is even more preferred to employ from 10 to 40 mg/kg of animal body weight of the benzimidazole compound along with from 2½ to 30 mg/kg of animal body weight of the salicylanilide compound. Still more preferred is the administration of from 20 to 35 mg/kg of animal body weight of the benzimidazole along with from 5 to 15 mg/kg of animal body weight of the salicylanilide. The amount of each compound in the composition may be adjusted such that the compounds are administered in quantities within the above listed dose ranges. Gradually, however, the composition ratio is adjusted such that the 3'-chloro-4'-(p-chlorophenoxy)-3,5-diiodosalicylanilide is present to the extent of from 5 to 150% by weight of the 5-isopropoxycarbonlyamino-2-(4'-thiazolyl)-benzimidazole. It is even more preferred to have the salicylanilide present in the composition to the extent of from 25 to 100%. These ratios may, however, be exceeded if necessary if a helminthic infection is present which is difficult to eradicate and requires more of one compound or the other.

The instant combination of compounds has been tested in various animals infected with helminths and the benefits of such a combination demonstrated. In one such test in sheep it was shown that an infection of *Haemonchus contortus* was reduced by 88% in the adult stage by administration of 10 mg/kg of 3'-chloro-4'-(p-chlorophenoxy)-3,5-diiodosalicylanilide. In a separate test against the same infection 5-isopropoxycarbonylamino-2-(4'-thiazolyl)-benzimidazole at 10 mg/kg was observed to have no effect on the infection. When 10 mg/kg of each of the compounds were combined and tested against the same infection the reduction was observed to be 98% or almost complete reduction. Thus the effects of the two compounds is seen to be more than merely additive.

The following examples are given for the purpose of illustration and not by way of limitation.

EXAMPLE 1

5-Isopropoxycarbonylamino-2-(4'-thiazolyl)-Benzimidazole 2.60 G. of isopropyl chloroformate are added at room temperature to a stirred solution of 4.32 g. of 5-amino-2-(4'-thiazolyl)-benzimidazole in 15 ml. of pyridine. The resulting mixture is stirred at room temperature for 2 hours then poured onto ice and the mixture diluted with water to a volume of about 300 ml. A dark oil separates and is recovered by decanting the mother liquors. The oil is washed with water and then dissolved in methanol. The methanolic solution is filtered, evaporated to near dryness in vacuo and the residue dried by adding benzene and removing the benzene by distillation. The residue is then crystallized from methanol-ether-petroleum ether, the crystals are separated and air dried to give 5-isopropoxycarbonylamino-2-(4'-thiazolyl)-benzimidazole.

EXAMPLE 2

3,5-Diiodo-3'-Chloro-4'-(p-chlorophenoxy)-Salicylanilide

A mixture of 31.0 g. of 4-amino-2,4'-dichlorobiphenyl ether, 47.4 g. of 3,5-diiodo salicylic acid, and 4.3 ml. of phosphorus trichloride in 235 ml. of chlorobenzene is refluxed for 3 hours. The hot solution is decanted from some insoluble residue and the crude product settles out of solution upon cooling to room temperature. Upon recrystallization from benzene, 27.8 g. of 3,5-diiodo-3'-chloro-4'-(p-chlorophenoxy)-salicylanilide, m.p. 168°–170°C. is obtained.

EXAMPLE 3

The following ingredients are combined in the following fashion in order to form a drench composition suitable for administration to larger animals such as sheep or cattle.

| Ingredient | Percent (w/v) |
|---|---|
| 5-isopropoxycarbonylamino-2-(4'-thiazolyl)-benzimidazole | 12.50 |

-continued

| Ingredient | Percent (w/v) |
|---|---|
| 3'-chloro-4'-(p-chlorophenoxy)-3,5-diiodosalicylanilide | 7.50 |
| Methylparaben USP | 0.18 |
| Propylparaben USP | 0.02 |
| Dioctyl Sodium Sulfasuccinate USP | 0.50 |
| Glycerine USP | 10.00 (v/v) |
| Antifoam A.F. Emulsion (Dow-Corning Co.) | 0.10 |
| Xanthan Gum | 0.30 |
| Water, Purified q.s. ad. | 100.00 |

In a suitable mixing tank the methylparaben and propylparaben are dissolved in a mixture of glycerine and water. Dioctyl sodium sulfasuccinate is dissolved in the vehicle. The Antifoam A.F. emulsion, which was previously dispersed in water, is also added and thoroughly distributed. The Xanthan Gum is then added and dissolved. The active ingredients are added and dispersed. The suspension is then mixed throughly, homogenized and brought to the final volume.

Alternatively all of the solid ingredients may be combined in the form of a dry premix and combined with the liquid ingredients just prior to administration.

EXAMPLE 4

A bolus containing -5-isopropoxycarbonylamino-2-(4'-thiazolyl)-benzimidazole and 3'-chloro-4'-(p-chlorophenoxy)-3,5-diiodosalicylanilide suitable for oral administration to domesticated animals of about 100 pounds of body weight is prepared from the following ingredients:

| Ingredient | Amount |
|---|---|
| 5-isopropoxycarbonylamino-2-(4'-thiazolyl)-benzimidazole | 3.3 g. |
| 3'-chloro-4'-(p-chlorophenoxy)-3,5-diiodosalicylanilide | 1.5 |
| Dicalcium phosphate | 3.0 |
| Starch | 0.535 |
| Guar gum | 0.15 |
| Talc | 0.14 |
| Magnesium Stearate | 0.04 |
| | 8.665 |

The dicalcium phosphate is thoroughly mixed with the 5-isopropoxycarbonylamino-2-(4'-thiazolyl)-benzimidazole and the 3'-chloro-4'-(p-chlorophenoxy)-3,5-diiodosalicylanilide and the mixture reduced to a particle size finer than 60 mesh. To the mixture is added 0.330 g. of starch in the form of an aqueous starch paste and the resulting mixture granulated in the usual manner. The granules are then passed through a No. 10 mesh screen and dried at 40°–55°C. for about 18 hours, and the dried material then passed through a No. 16 mesh screen. The guar gum and the balance of the starch are added and the mixture thoroughly blended. The remainder of the ingredients are then added and the whole throughly mixed and compressed.

What is claimed is:

1. A composition for the treatment of Haemonchus infections which comprises from 0.001 to 95% by weight of a combination of 5-isopropoxycarbonylamino-2-(4'-thiazolyl)benzimidazole and about 100% by weight of 3'-chloro-4'-(p-chlorophenoxy)-3,5-diiodosalicylanilide and an inert carrier.

2. The composition of claim 1 which is a dry predrench composition and which contains from 30 to 95% by weight of said compounds.

3. The composition of claim 1 which is a drench composition and which contains from 10 to 50% by weight of said compounds.

4. The composition of claim 3 in which said compounds are present to the extent of from 15 to 50% by weight.

5. The composition of claim 1 which is a feed premix and which contains from 5 to 50% by weight of said compounds.

6. The composition of claim 5 in which said compounds are present to the extent of from 10 to 30% by weight.

7. The composition of claim 1 which is a finished feed product and which contains from 0.001 to 25% by weight of said compounds.

8. A method for the treatment of Haemonchus infections which comprises orally administering to an animal infected with Haemonchus an effective amount of a combination of 5-isopropoxycarbonylamino-2-(4'-thiazolyl) benzimidazole and about 100% by weight thereof of 3'-chloro-4'-(p-chlorophenoxy)3,5-diiodosalicylanilide.

* * * * *